(12) United States Patent  
Nishio et al.

(10) Patent No.: US 8,680,487 B2  
(45) Date of Patent: Mar. 25, 2014

(54) CHARGED PARTICLE DOSE SIMULATION DEVICE, CHARGED PARTICLE BEAM IRRADIATION DEVICE, CHARGED PARTICLE DOSE SIMULATION METHOD, AND CHARGED PARTICLE BEAM IRRADIATION METHOD

(75) Inventors: Teiji Nishio, Kashiwa (JP); Yuusuke Egashira, Tokyo (JP); Manabu Yamada, Tokyo (JP)

(73) Assignees: National Cancer Center, Tokyo (JP); Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 13/267,510

(22) Filed: Oct. 6, 2011

(65) Prior Publication Data

US 2013/0087721 A1  Apr. 11, 2013

(51) Int. Cl.  
*A61N 5/00* (2006.01)

(52) U.S. Cl.  
USPC ...................................... 250/492.1

(58) Field of Classification Search  
None  
See application file for complete search history.

(56) References Cited

U.S. PATENT DOCUMENTS

| | | | |
|---|---|---|---|
| 2002/0087298 A1* | 7/2002 | Ito et al. | 703/14 |
| 2003/0204126 A1* | 10/2003 | Rivard | 600/3 |
| 2004/0099636 A1* | 5/2004 | Scipioni | 216/66 |
| 2005/0116172 A1* | 6/2005 | Trinkaus et al. | 250/363.02 |
| 2005/0197564 A1* | 9/2005 | Dempsey | 600/411 |
| 2006/0145088 A1* | 7/2006 | Ma | 250/396 ML |
| 2007/0034812 A1* | 2/2007 | Ma et al. | 250/492.21 |
| 2007/0084474 A1* | 4/2007 | Rivard | 128/898 |
| 2008/0049896 A1* | 2/2008 | Kuduvalli | 378/65 |
| 2008/0317204 A1* | 12/2008 | Sumanaweera et al. | 378/65 |
| 2009/0050819 A1* | 2/2009 | Ma et al. | 250/396 ML |
| 2009/0161826 A1* | 6/2009 | Gertner et al. | 378/65 |
| 2009/0252292 A1* | 10/2009 | Simon et al. | 378/65 |
| 2009/0257557 A1* | 10/2009 | Sumanaweera et al. | 378/65 |
| 2010/0082294 A1* | 4/2010 | Adnani | 702/182 |
| 2010/0113911 A1* | 5/2010 | Dempsey | 600/411 |
| 2010/0260317 A1* | 10/2010 | Chang et al. | 378/62 |

(Continued)

FOREIGN PATENT DOCUMENTS

| | | |
|---|---|---|
| JP | 2000-126318 A | 5/2000 |
| JP | 2007-531566 A | 11/2007 |

OTHER PUBLICATIONS

Kanematsu et al., ("Computational Modeling of Beam-Customization Devices for Heavy-Charged-Particle Radiotherapy", Phys. Med. Biol. 53 (2008) 3113-3127, pp. 3113-3127).*

(Continued)

*Primary Examiner* — Andrew Smyth  
(74) *Attorney, Agent, or Firm* — Squire Sanders (US) LLP

(57) ABSTRACT

A simulation device includes an input unit which receives an input of simulation data including material information of the irradiation target and irradiation information of a charged particle beam, and an arithmetic unit which calculates the dose distribution of the charged particle beam in the irradiation target on the basis of simulation data received by the input unit and the dose distribution kernel. The arithmetic unit segments the charged particle beam spread to a predetermined range at an intermediate portion in the traveling direction of the charged particle beam, hypothesizes a plurality of virtual shapes having conical spread with a segmented position as a start point, and calculates the dose distribution of the charged particle beam in the irradiation target on the basis of simulation data received by the input unit and a plurality of virtual shapes of the charged particle beam.

7 Claims, 14 Drawing Sheets

(56) References Cited

U.S. PATENT DOCUMENTS

| | | | |
|---|---|---|---|
| 2011/0081001 A1* | 4/2011 | Gertner et al. | 378/65 |
| 2011/0101228 A1* | 5/2011 | Hamby et al. | 250/362 |
| 2011/0137158 A1* | 6/2011 | Sumanaweera et al. | 600/427 |
| 2011/0184283 A1* | 7/2011 | Rivard | 600/436 |
| 2012/0022363 A1* | 1/2012 | Dempsey | 600/411 |

OTHER PUBLICATIONS

Martin Soukup et al., "A Pencil Beam Algorithm for Intensity Modulated Proton Therapy Derived from Monte Carlo Simulations", Physics in Medicine and Biology, Taylor and Francis Ltd. London, GB, vol. 50, No. 21, Nov. 2005, pp. 5089-5104.

Barbara Schaffner et al., "Dose Calculation Models for Proton Treatment Planning Using a Dynamic Beam Delivery System: an Attempt to Include Density Heterogeneity Effects in the Analytical Dose Calculation", Physics in Medicine and Biology, vol. 44, No. 1, Jan. 1, 1999, pp. 27-41.

Nobuyuki Kanematsu et al., "Computational Modeling of Beam-Customization Devices for Heavy-Charged-Particle Radiotherapy; Modelin of Beam-Customization Devices for Particle Radiotherapy", Taylor and Francis Ltd. London, GB, vol. 53, No. 12, Jun. 21, 2008, pp. 3113-3127.

European Search Report application No. 11008101.5 dated Apr. 19, 2012.

Harald Paganetti et al., "Clinical Implementation of Full Monte Carlo Dose Calculation in Proton Beam Therapy", Physics in Medicine and Biology, 2008, pp. 4825-4853.

Harald Paganetti, "Dose to Water Versus Dose to Medium in Proton Beam Therapy", Physics in Medicine and Biology, 2009, pp. 4399-4421.

Nobuyuki Kanematsu et al., "Dynamic Splitting of Gaussian Pencil Beams in Heterogeneity-Correction Algorithms for Radiotherapy with Heavy Charged Particles", Physics in Medicine and Biology, 2009, pp. 2015-2027.

Linda Hong et al., "A Pencil Beam Algorithm for Proton Dose Calculations", Phys. Med. Biol., 1996, pp. 1305-1329.

\* cited by examiner

*Fig.8*
(a) 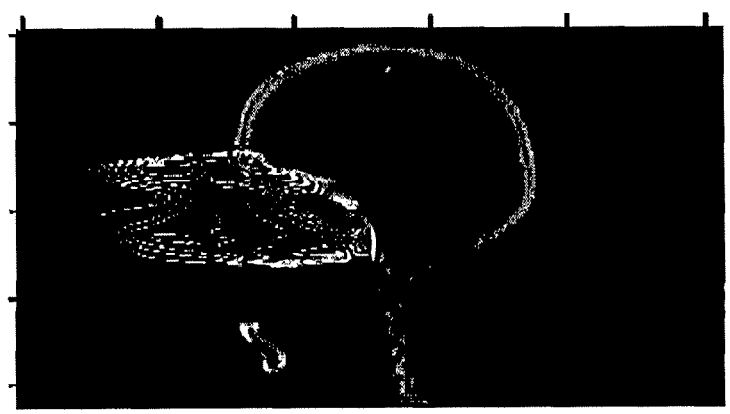
PBA
(b) 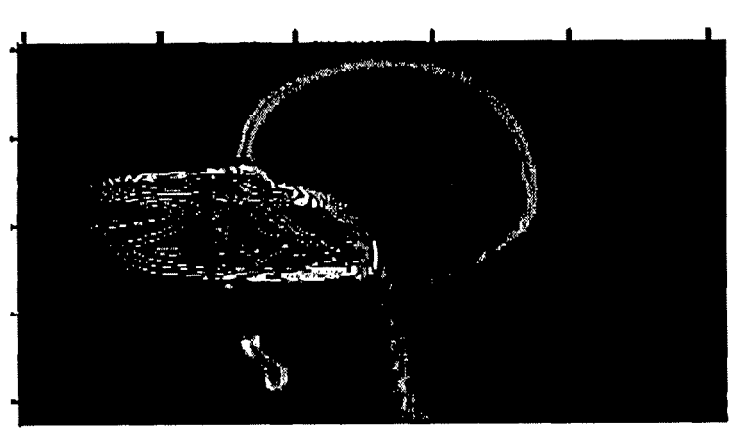
DMS-PBA

CHARGED PARTICLE DOSE SIMULATION DEVICE, CHARGED PARTICLE BEAM IRRADIATION DEVICE, CHARGED PARTICLE DOSE SIMULATION METHOD, AND CHARGED PARTICLE BEAM IRRADIATION METHOD

BACKGROUND

1. Technical Field

The present invention relates to a charged particle dose simulation device which performs a simulation on the dose distribution of a charged particle beam in an irradiation target when irradiating a charged particle beam, such as a proton beam, onto the irradiation target, a charged particle beam irradiation device, a charged particle dose simulation method, and a charged particle beam irradiation method.

2. Description of the Related Art

A proton therapy apparatus is known which irradiates a charged particle beam, such as a proton beam, to treat a tumor. In this tumor therapy, it is necessary to draw up an irradiation plan of an absolute dose, a dose distribution, an irradiation position, and the like depending on the shape or position of a tumor and to irradiate the charged particle beam with good precision in accordance with the irradiation plan. In drawing up the irradiation plan, the irradiation conditions of a proton beam or the like are input to a simulation device mounted in the proton therapy apparatus or the like to calculate a dose distribution in advance, and a simulation is performed as to whether or not a proton beam is accurately irradiated onto a tumor on the basis of the dose distribution. As the method of calculating the dose distribution, for example, a method, called Monte Carlo simulation or pencil beam algorithm (PBA), is known (see the related art).

SUMMARY

An embodiment of the invention provides a simulation device which supposes when a charged particle beam is irradiated onto an irradiation target, hypothesizes the charged particle beam as a virtual shape having conical spread, and simulates the dose distribution of a charged particle beam in the irradiation target using a dose distribution kernel which derives the spread of the charged particle beam in the irradiation target. The simulation device includes an input unit which receives an input of simulation data including material information of the irradiation target and irradiation information of the charged particle beam, and an arithmetic unit which calculates the dose distribution of the charged particle beam in the irradiation target on the basis of simulation data received by the input unit and the dose distribution kernel. The arithmetic unit segments the charged particle beam spread to a predetermined range at an intermediate portion in the traveling direction of the charged particle beam, hypothesizes a plurality of virtual shapes having conical spread with a segmented position as a start point, and calculates the dose distribution of the charged particle beam in the irradiation target on the basis of simulation data received by the input unit and a plurality of virtual shapes of the charged particle beam.

Another embodiment of the invention provides a charged particle beam irradiation device including the simulation device. According to the embodiment of the invention, it becomes possible to irradiate the charged particle beam on the basis of the dose distribution of the charged particle beam quickly calculated by the simulation device.

Another embodiment of the invention provides a simulation method which supposes when a charged particle beam is irradiated onto an irradiation target, hypothesizes the charged particle beam as a virtual shape having conical spread, and simulates the dose distribution of a charged particle beam in the irradiation target using a dose distribution kernel which derives the spread of the charged particle beam in the irradiation target. The simulation method includes an irradiation target information acquisition step of acquiring material information of the irradiation target, an irradiation information setting step of determining irradiation information of the charged particle beam, and a simulation step of segmenting the charged particle beam spread to a predetermined range at an intermediate portion in the traveling direction of the charged particle beam on the basis of the irradiation information determined in the irradiation information setting step and the dose distribution kernel, hypothesizing a plurality of virtual shapes having conical spread with a segmented position as a start point, and determining the dose distribution of the charged particle beam in the irradiation target on the basis of the material information acquired in the irradiation target information acquisition step and a plurality of virtual shapes of the charged particle beam.

Another embodiment of the invention provides a charged particle beam irradiation method which irradiates a charged particle beam on the basis of the dose distribution of the charged particle beam calculated by the above-described simulation method. With the embodiment of the invention, it becomes possible to irradiate the charged particle beam on the basis of the dose distribution of the charged particle beam quickly calculated by the simulation method.

BRIEF DESCRIPTION OF THE DRAWINGS

FIG. 6A is an explanatory view schematically showing PBA, and FIG. 6B is an explanatory view schematically showing DMS-PBA.

FIG. 7A is a diagram showing a difference between a DMS-PBA method and a PBA method of the related art in the form of an isodose line, FIG. 7B is a graph showing dose distributions of a DMS-PBA method and a PBA method of the related art at a depth of 0 mm, and FIG. 7C is a graph showing dose distributions at a depth of 115 mm.

FIGS. 8A and 8B are diagrams showing dose distributions by comparison using a clinical image (sagittal section), specifically, FIG. 8A shows an example of an image of a dose distribution obtained by a PBA method in the form of an isodose line, and FIG. 8B shows an example of an image of a dose distribution obtained by a DMS-PBA in the form of an isodose line.

FIG. 9A shows an example of an image of a dose distribution obtained by a PEA method in the form of an isodose line, and FIG. 9B shows an example of an image of a dose distribution obtained by a DMS-PBA in the form of an isodose line.

DETAILED DESCRIPTION

Figure 1:
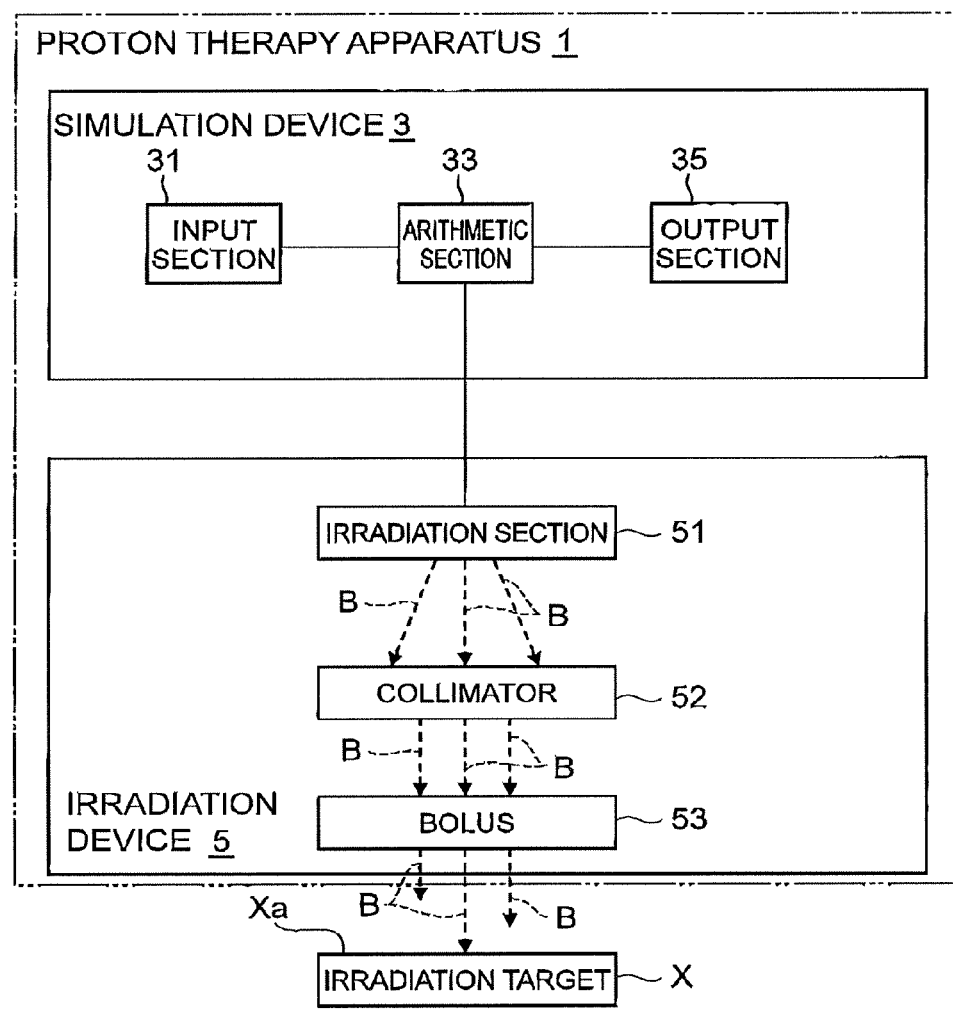
FIG. 1 is an explanatory view of a proton therapy apparatus in which a simulation device according to an embodiment of the invention is mounted.

In the above-described Monte Carlo simulation, since the dose distribution is calculated through statistical processing, precision is high, but there is a large burden of arithmetic processing, and the simulation requires a period of several days, resulting in a lack of practical utility. Meanwhile, in the PEA, precision is invariably apt to be degraded compared to the Monte Carlo simulation, and it is difficult to secure desired precision.

It is desirable to provide a charged particle dose simulation device, a charged particle beam irradiation device, a charged particle dose simulation method, and a charged particle beam irradiation method capable of reducing a burden of arithmetic processing while suppressing degradation in precision to quickly calculate the dose distribution of a charged particle beam.

When an irradiation target is made of only a predetermined material, even in the PBA of the related art, comparatively high precision can be expected. However, since an actual irradiation target is made by complicatedly combining various materials, in the PBA of the related art, it is difficult to calculate the dose distribution of the charged particle beam with good precision. Meanwhile, according to the embodiment of the invention, a conical virtual shape hypothesized as a charged particle beam is appropriately segmented and hypothesized as a plurality of virtual shapes, such that it becomes possible to cope with a configuration in which the segmented virtual shapes are complicatedly combined and also to calculate the dose distribution of the charged particle beam. Thus, it is effective for improving the precision of the dose distribution. With the embodiment of the invention, after a charged particle beam is hypothesized as a conical virtual shape, the dose distribution of the charged particle beam is obtained, making it possible to reduce a burden of arithmetic processing compared to the Monte Carlo simulation in which the dose distribution is derived through statistical arithmetic processing. As a result, it becomes possible to reduce a burden of arithmetic processing while suppressing degradation in precision to quickly calculate the dose distribution.

A position where the charged particle beam is segmented may be a position immediately before the charged particle beam enters the irradiation target. It is possible to segment the charged particle beam into a plurality of virtual shapes to correspond to the internal structure immediately before the charged particle beam enters the irradiation target, making it easy to further improve precision in calculating the dose distribution of the charged particle beam.

The simulation device may further include an output unit which provides notification of the dose distribution calculated by the arithmetic unit. Text information, image information, sound information, or the like which can be viewed or heard by an operator is notified from the output unit, such that it is possible for the operator to easily recognize the dose distribution of the charged particle dose as a simulation result.

The output unit may provide notification of the dose distribution in the form of an isodose line or isodose surface. Notification is made in the form of an isodose line or isodose surface, making it possible to easily recognize the magnitude of the dose. According to the embodiment of the invention, it becomes possible to reduce a burden of arithmetic processing while suppressing degradation in precision to quickly calculate the dose distribution.

Hereinafter, an exemplary embodiment of the invention will be described with reference to the drawings.

In irradiating a proton beam (charged particle beam) to treat a tumor (cancer lesion), an irradiation plan of an absolute dose, a dose distribution, an irradiation position or the like is drawn up depending on the shape or position of the tumor, and the proton beam is irradiated in accordance with the irradiation plan. As shown in FIG. 1, a proton therapy apparatus (charged particle beam irradiation device) 1 includes a simulation device (charged particle dose simulation device) 3 which draws up an irradiation plan, and an irradiation device 5 which irradiates a proton beam B onto an irradiation target X, such as a patient, in accordance with a simulation result.

The irradiation device 5 includes an irradiation section 51 which irradiates the proton beam B toward the irradiation target X, a collimator 52 which adjusts the irradiation range of the proton beam B, and a bolus 53 which adjusts the traveling distance of the proton beam B depending on the shape of the cancer lesion. The material of the bolus 53 is polyethylene or the like. Actual irradiation by the irradiation device 5 is done on the basis of input manipulation of the irradiation device 5 by the operator.

Figure 2:
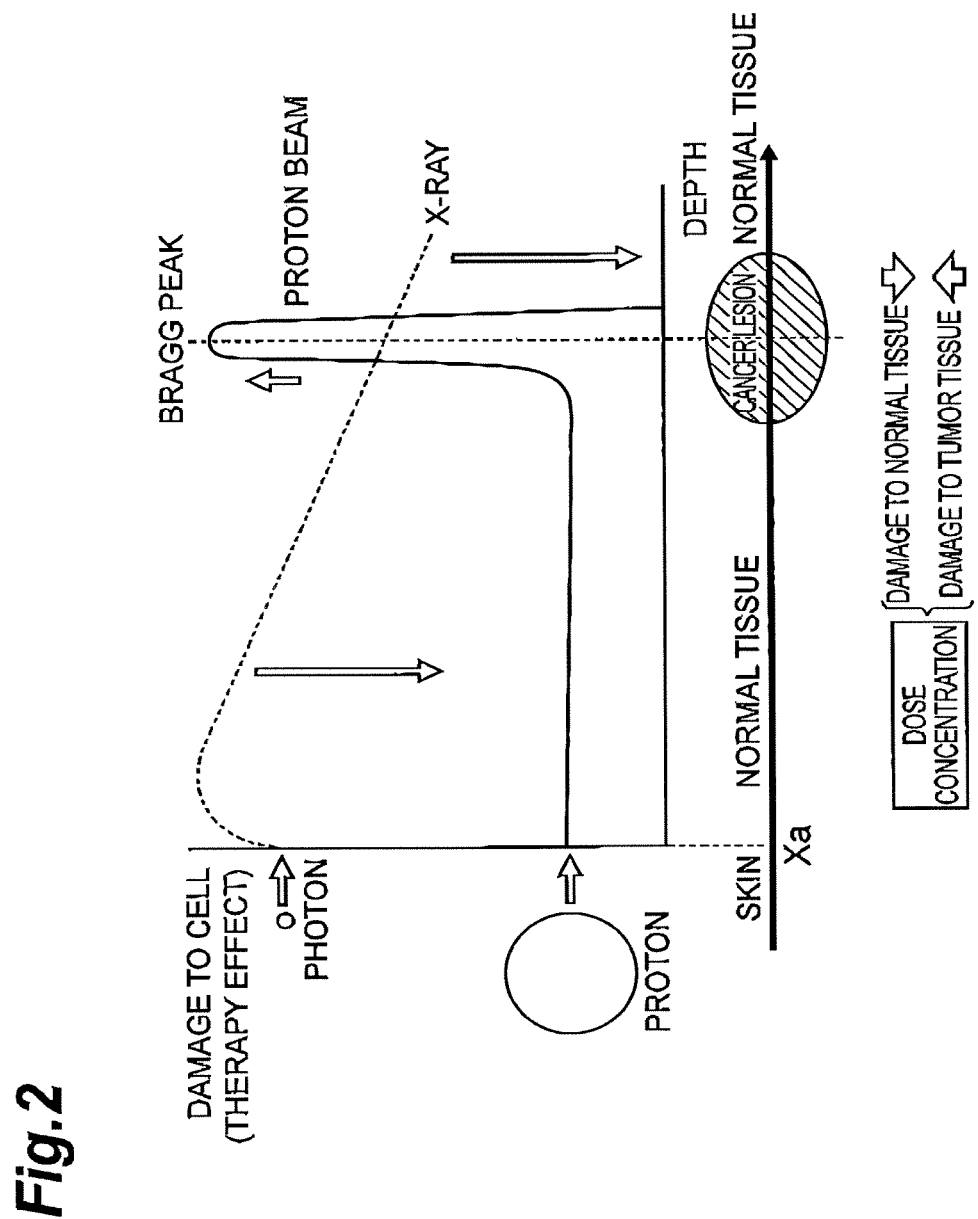
FIG. 2 is an explanatory view graphically showing the effect of proton therapy.

As shown in FIG. 2, a photon beam reaches a peak (having maximum therapy effect) maximum damage to a cell immediately after being incident on the skin (body surface Xa) of a patient (before reaching a cancer lesion) and gradually decreases. Meanwhile, in the case of a heavy charged particle, such as a proton beam, a maximum portion called a Bragg peak appears at a predetermined depth. Thus, the shape or the like of the bolus 53 through which the proton beam B passes is appropriately adjusted to adjust the depth at which the Bragg peak appears, making it possible to suppress damage to a normal tissue and to increase damage to a tumor tissue (cancer lesion).

The simulation device 3 (see FIG. 1) includes a central processing unit. The central processing unit has a CPU, a RAM, a ROM, and the like as a hardware configuration, and has an input section (input unit) 31, an arithmetic section (arithmetic unit) 33, and an output section (output unit) 35 as a functional configuration.

The input section 31 is a manipulation device, such as a touch panel, a keyboard, or a mouse, and receives an input of data based on manipulation by the operator. The input section 31 receives, for example, image data including a cancer lesion captured by a CT (Computed Tomography) for therapy, data relating to an irradiation region, and irradiation parameter data. Irradiation parameter data refers to, for example, data relating to an irradiation direction, an angle of a patient bed, or the like. In this embodiment, image data (CT image data for therapy) acquired by the CT for therapy corresponds to material information of the irradiation target X, and data relating to the irradiation region and irradiation parameter data correspond to irradiation information of the charged particle beam. Hereinafter, these kinds of data are collectively referred to as simulation data.

The arithmetic section 33 has a function of supposing when the proton beam B is irradiated onto the irradiation target X, hypothesizing the proton beam B as a virtual shape having conical (pencil beam shape) spread, and simulating the dose distribution of the proton beam B in the irradiation target X by using a dose distribution kernel which derives the spread of the proton beam B in the irradiation target X. Here, although in the related art, the method of calculating the dose distribution is, for example, a pencil-beam method (PBA method), in this embodiment, dose distribution computation is carried out by a delta-function multi segmented PBA method (DMS-PBA method) further advanced from the PBA method. Hereinafter, the PEA method will be schematically described, and then the DMS-PBA method will be described in detail.

Figure 3:
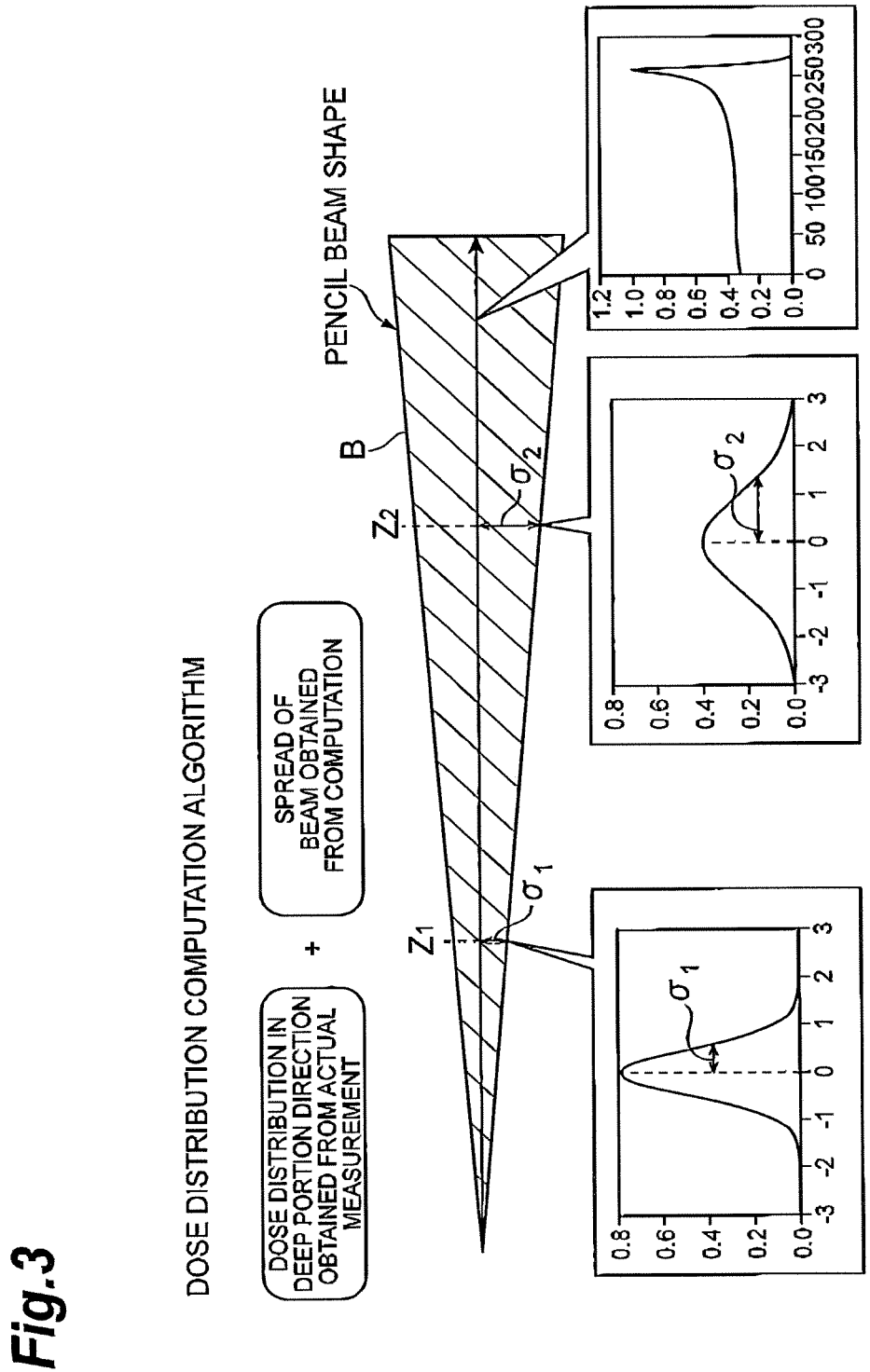
FIG. 3 is an explanatory view schematically showing the concept of a dose distribution computation algorithm.

The PEA method refers to the method in which the proton beam B is used to resemble a pencil beam shape, and computation is carried out by using a dose distribution kernel taking into consideration the spread by multiple Coulomb scattering of the proton beam B in a material. Specifically, as shown in FIG. 3, the dose distribution in a deep portion direction from an irradiation point is acquired by actual measurement, and the dose distribution at a predetermined spot in the traveling direction of the proton beam B is derived taking into consideration the spread of a beam obtained from predetermined computation (Gaussian approximation). For example, the spread at a spot $Z_1$ is obtained as spread $\sigma_1$ by Gaussian approximation, and the spread at a spot $Z_2$ is obtained as spread $\sigma_2$ by Gaussian approximation.

According to the PBA method of the related art, it is advantageous in that the dose distribution of the proton beam B can be derived in a computation time of about several minutes, but there is room for improvement because computation precision is degraded depending on the presence/absence of a heterogeneous material (for example, a bone of a patient or the like) in an irradiation range.

The DMS-PBA method achieves the improvement in precision as well as the reduction in the computation time which is an advantage of the PBA method. The DMS-PBA method has at least two characteristic points. The first characteristic point is dose distribution computation taking into consideration scattering from the bolus 53 by surface map analysis in the body surface Xa of the irradiation target (patient or the like) X. The second characteristic point is dose distribution computation of high resolution by a beamlet Ba to be emitted with the body surface Xa as a start point.

Figure 4:
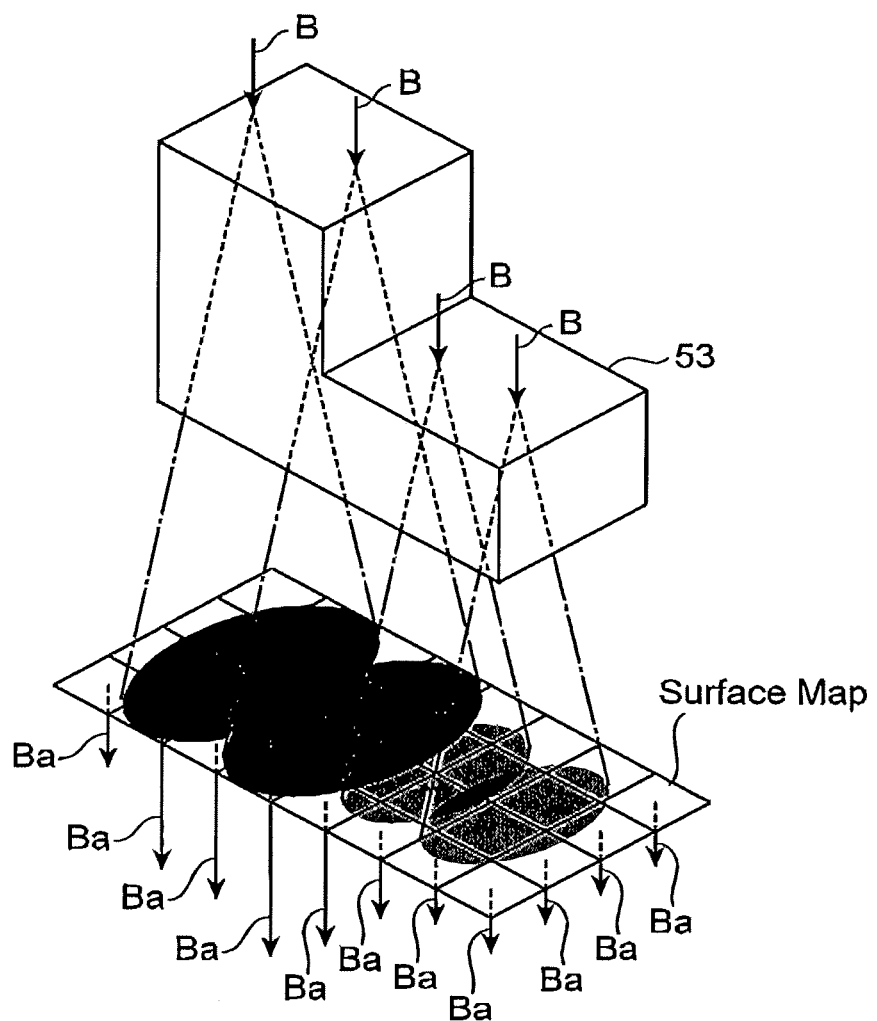
FIG. 4 is an explanatory view schematically showing the concept of a DMS-PBA method.
Figure 5:
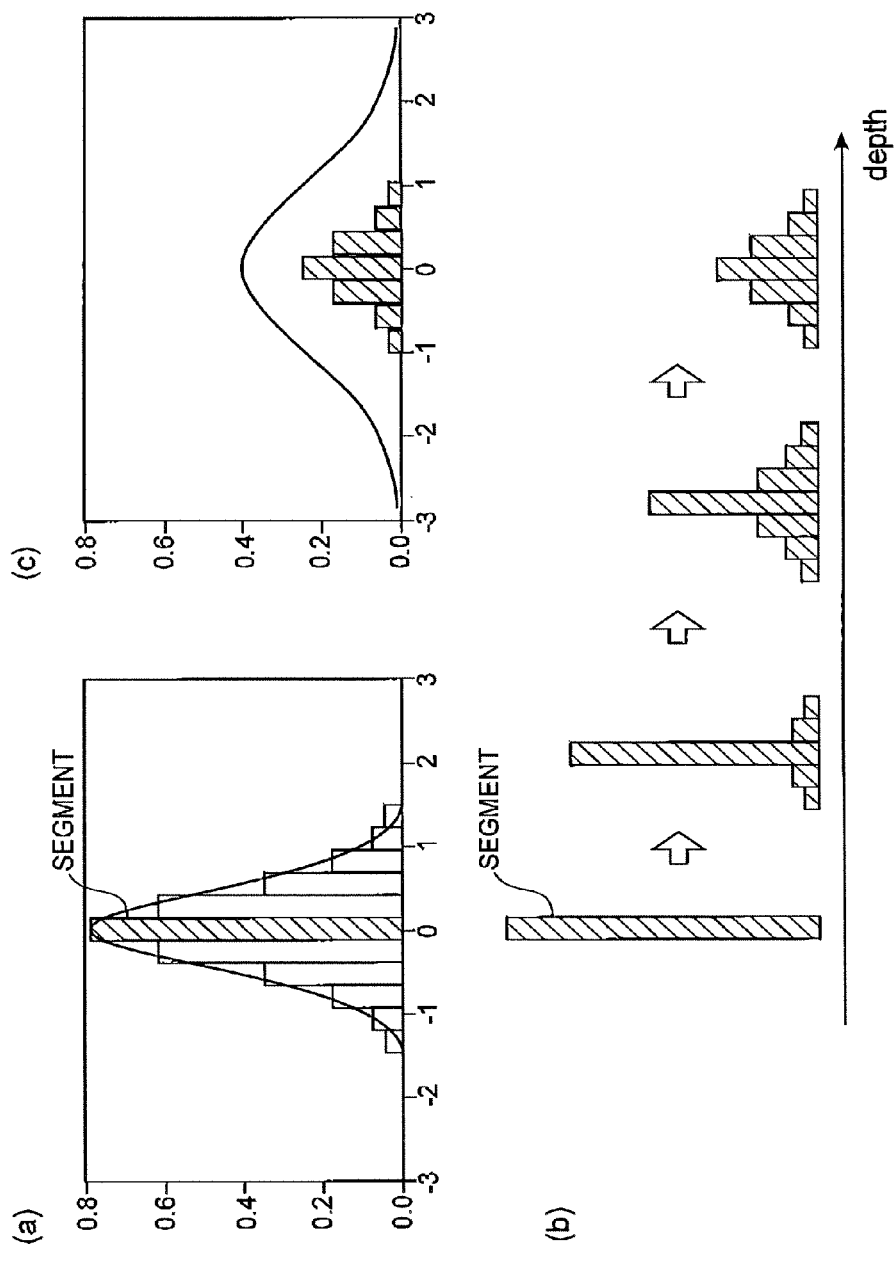
FIGS. 5A to 5C are explanatory views as to segmentation of beamlets in a DMS-PBA method.

The characteristics of the DMS-PBA method will be conceptually described with reference to FIGS. 4 and 5. FIG. 4 is an explanatory view schematically showing the concept of the DMS-PBA method. FIGS. 5A to 5C are explanatory views as to segmentation of a beam in the DMS-PBA method. As shown in FIG. 4, the proton beam (beam) B input to the bolus 53 or the like travels while generating spread by lateral multiple Coulomb scattering and reaches the body surface Xa. Here, lateral emittance of the beam B to the body surface Xa is calculated. This computation is the same as in the PBA of the related art.

Next, a surface map to the body surface Xa is created. The surface map is obtained by mapping the total intensity (weight) of the beams B, residual tracks, and the number of beams B having different residual tracks on each computational grid in the body surface Xa. For example, when the bolus 53 is hypothesized as a block body having an L-shaped section, the residual track in the body surface Xa of the beam B having passed through a thick portion becomes smaller than the residual track in the body surface Xa of the beam B having passed through a thin portion. In a region where the beam B having passed through a thick portion and the beam B having passed through a thin portion overlap each other in the body surface Xa, the dose (intensity) becomes larger than a region where the beam B having passed through a thick portion and the beam B having passed through a thin portion do not overlap each other. The surface map in the body surface Xa is created in consideration of these components. The above is dose distribution computation taking into consideration scattering from the bolus 53 by surface map analysis in the body surface Xa of the irradiation target X, and is the first characteristic of the DMS-PBA method. A residual track is a track corresponding to kinetic energy of a proton beam.

Next, the surface map is segmented, and the initial conditions of a plurality of proton beams (hereinafter, referred to as "beamlets") Ba virtually irradiated with each segmented component (hereinafter, referred to as "voxel") as a start point are determined. For example, the dose of the beamlets Ba is obtained by segmenting the dose distribution supposed to be incident on the body surface Xa in a delta function shape (see FIG. 5A). The size of the beamlet Ba in the voxel is hypothesized to be very small.

Next, the dose distribution computation by the beamlets B irradiated from the body surface Xa into the body is carried out. The dose distribution computation by the beamlets Ba will be conceptually described with reference to FIGS. 5A to 5C. FIG. 5A shows the lateral profile of the dose in the body surface Xa. As shown in FIG. 5A, the dose of the beamlets Ba is obtained by segmentation of the dose distribution described above. If it is hypothesized that the beamlets (segments) Ba are irradiated into the body, each segment spreads with an increasing depth (see FIG. 5B). The dose distribution at an arbitrary depth in the body is derived by overlapping the segments (see FIG. 5C). FIG. 5C shows the lateral profile of the dose in the body.

All the beamlets Ba are integrated to make it possible to calculate the dose distribution in the body. The above is the dose distribution computation of high resolution by the beamlets Ba emitted with the body surface Xa as a start point, and is the second characteristic of the DMS-PBA method. Specific computation of a beam size by the DMS-PBA method is based on the following expression (1).

[Equation 1]

$$\sigma_{dms}^2 = \sigma_{suf}^2 + \left\{2d\left(\frac{t}{2} + g\right) + d^2\right\}\sigma_\theta^2 + \sigma_{pt}^2 \quad (1)$$

$$\sigma_{init} = \sigma_{suf} = \frac{VOXELSIZE}{2 \times THRESHOLD}$$

$$^\dagger \sigma_\theta(z) = 14.1\left[1 + \frac{1}{9}\log_{10}\left(\frac{z}{L_R}\right)\right]\left[\int_-^z \left(\frac{1}{pv}\right)^2 \frac{dz'}{L_R}\right]^{1/2}$$

$$^\dagger \sigma_{pt}(z) = 14.1\left[1 + \frac{1}{9}\log_{10}\left(\frac{z}{L_R}\right)\right]\left[\int_0^z \left(\frac{z-t}{pv}\right)^2 \frac{\rho}{L_R}dt\right]^{1/2}$$

$\sigma_{init}$: initial beam size
$\sigma_{dms}$: beam size by DMS-PBA
d: depth based on body surface
t: bolus thickness
g: air-gap from bolus to body surface
$\sigma_\theta$: scattering angle by bolus
$\sigma_{pt}$: scattering light in irradiation target (patient body)

Figure 6:
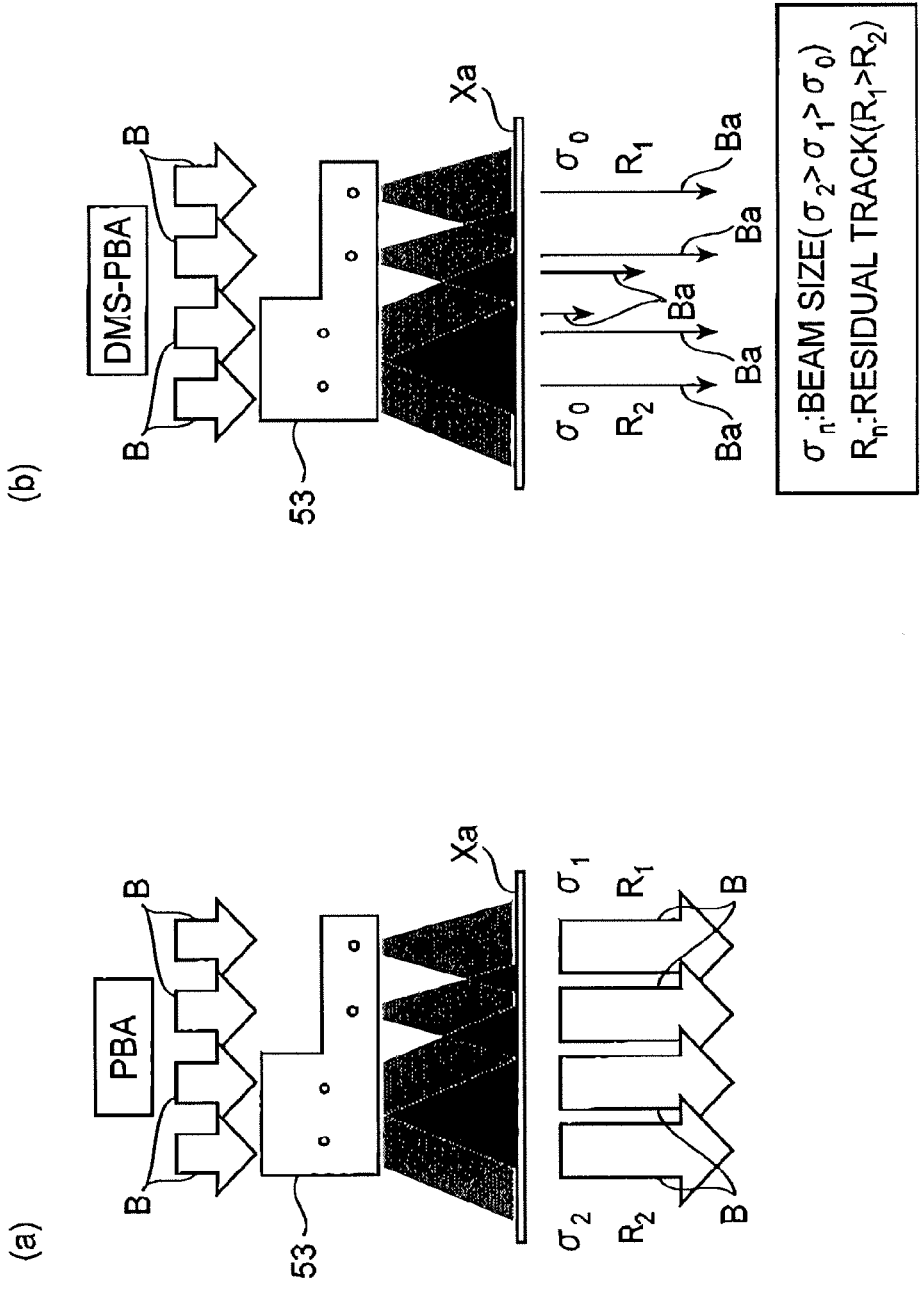
FIGS. 6A and 6B schematically show a difference between a DMS-PBA method and a PBA method of the related art, specifically.
Figure 7:
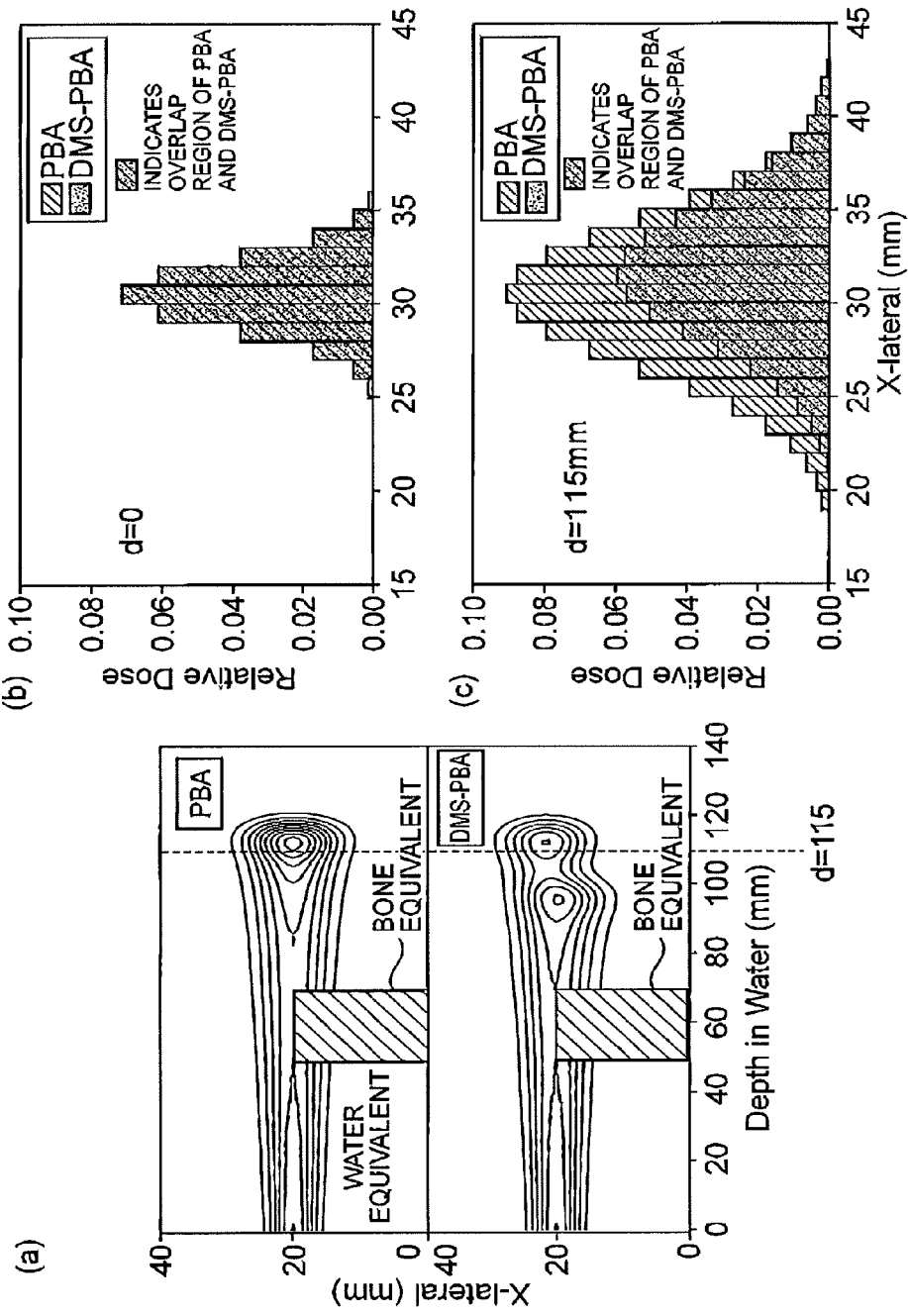
FIGS. 7A to 7C are diagrams showing a difference in a dose distribution between a DMS-PBA method and a PBA method of the related art, specifically.

Next, a difference between the PBA method and the DMS-PBA method will be described with reference to FIGS. 6A to 7C. FIG. 6A is an explanatory view schematically showing PBA, and FIG. 6B is an explanatory view schematically showing DMS-PBA. As shown in FIGS. 6A and 6B, in the PBA method, the beam B having reached the body surface Xa becomes the initial condition of the beam B irradiated into the body as it is. That is, in the PBA method, it is hypothesized that the beam B which has passed through the bolus 53 and reached the body surface Xa with the beam size $\sigma_1$ and $\sigma_2$ and the residual tracks $R_1$ and $R_2$ is irradiated into the body as it is. Meanwhile, in the DMS-PBA method, it is hypothesized that the beam B which has been input to the body surface Xa with the beam size $\sigma_1$ and $\sigma_2$ and the residual tracks $R_1$ and $R_2$ is segmented into a plurality of beamlets Ba having a beam size $\sigma_o$ far smaller than $\sigma_1$ and $\sigma_2$ in the body surface Xa, and each beamlet Ba is irradiated into the body.

FIGS. 7A to 7C show the calculation results of the dose distribution in the DMS-PBA method and the PBA method supposing that the beam B is irradiated onto the model of the irradiation target X in which a bone-equivalent material is arranged in a water-equivalent material. FIG. 7A is a diagram showing a difference between the DMS-PRA method and the PBA method in the form of an isodose line. FIG. 7B is a diagram showing the lateral profiles in the DMS-PBA method and the PBA method at a depth of 0 mm. FIG. 7C shows the lateral profiles of the DMS-PBA method and the PBA method at a depth of 115 mm.

As shown in FIG. 7B, the beam B has the same size and dose when the depth d is "0 mm", that is, in the body surface Xa. Meanwhile, as shown in FIG. 7C, when the depth d is "115 mm", there is a significant difference between the dose distribution obtained by the PBA method and the dose distribution obtained by the DMS-PBA method. This difference occurs because, in the PBA method, the dose distribution is calculated without taking into consideration the presence of a bone-equivalent material, but in the DMS-PBA method, the dose distribution is calculated taking into consideration the presence of a bone-equivalent material.

The output section 35 is an output device, such as a monitor or a speaker, and outputs (provides notification of) the simulation result in the arithmetic section as an image, which is visible by the operator or the like, or sound data. That is, the output section 35 receives dose distribution data based on the arithmetic result in the DMS-PBA method from the arithmetic section 33, combines a dose distribution image in the form of an isodose line or isodose surface with a CT image for therapy on the basis of received dose distribution data, and generates and displays (provides notification of) image data (image information) which is visible by the operator or the like.

Figure 9:
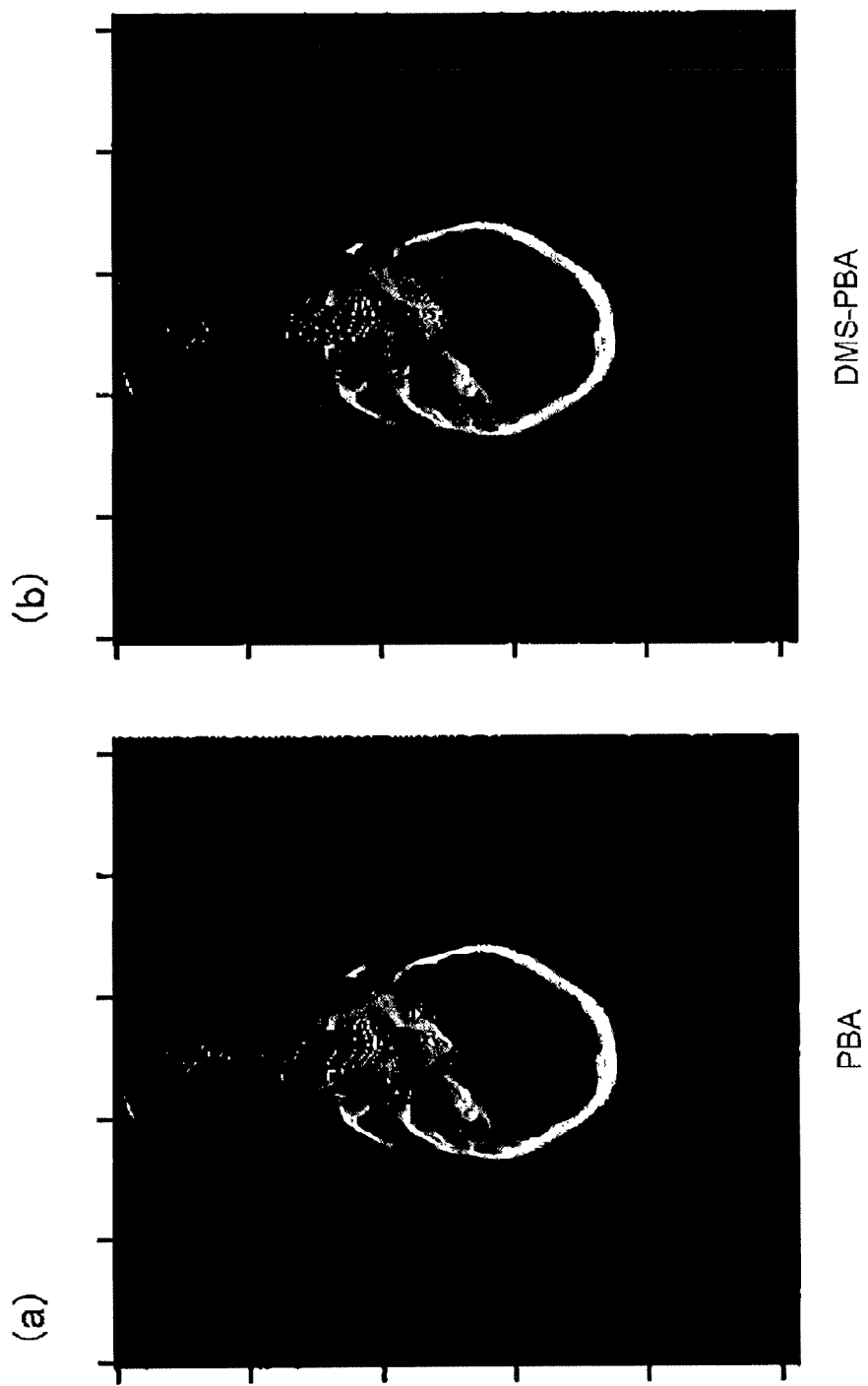
FIGS. 9A and 9B are diagrams showing dose distributions by comparison using a clinical image (axial section), specifically.

Here, image data displayed from the output section 35 will be described with reference to FIGS. 8A to 9B. FIGS. 8A to 9B show an example of an image of a dose distribution in the form of an isodose line. The output section 35 displays, for example, an image shown in FIG. 8B or 9B. FIGS. 8A and 9A show an image which represents a dose distribution derived by the PBA method. FIGS. 8B and 9B show an image which represents a dose distribution derived by the DMS-PBA method.

In comparison between a dose distribution image (FIG. 8A) in the PBA method and a dose distribution image (FIG. 8B) in the DMS-PBA method, the dose distribution image in the DMS-PBA method has a shape in which the isodose lines are complicatedly combined compared to the dose distribution image in the PBA method, and it is possible to infer that the dose distribution is calculated with good precision to correspond to a heterogeneous material. Similarly, as shown in FIG. 9, the dose distribution image (FIG. 9B) in the DMS-PBA method has a shape in which the isodose lines are complicated combined compared to the dose distribution image (FIG. 9A) in the PBA method, making it possible to infer that the dose distribution is calculated with good precision to correspond to a heterogeneous material.

Figure 10:
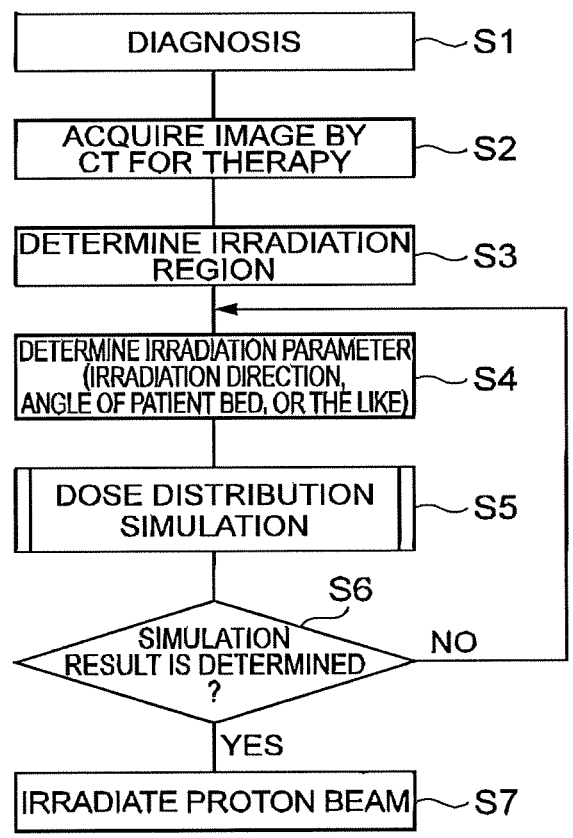
FIG. 10 is a flowchart showing a schematic procedure of proton therapy.
Figure 11:
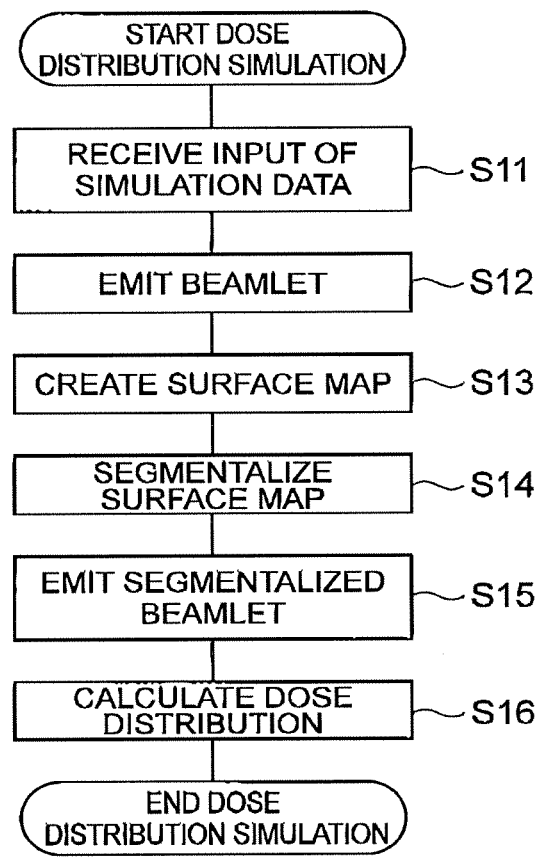
FIG. 11 is a flowchart showing an operation procedure of a dose distribution simulation.

Next, the outline of an actual proton therapy method will be described, and a dose distribution simulation method and a proton beam irradiation method (charged particle beam irradiation method) in the actual proton therapy method will be described with reference to FIGS. 10 and 11. FIG. 10 is a flowchart showing the schematic procedure of proton therapy and is a flowchart showing the operation procedure of a dose distribution simulation.

As shown in FIG. 10, diagnosis by an operator, such as a physician, is initially performed (Step S1), and thereafter, an image in the vicinity of a cancer lesion is acquired by the CT for therapy (Step S2). Next, an irradiation region is determined (Step S3), and irradiation parameters are determined (Step S4). The process for acquiring a CT image for therapy in Step S2 corresponds to an irradiation target X information acquisition process for acquiring material information of the irradiation target X. The processes for determining the irradiation region and the irradiation parameters in Steps S3 and S4 correspond to an irradiation information setting process for determining irradiation information of a charged particle beam.

Next, in the simulation device 3, processing relating to a dose distribution simulation is performed (Step S5), and a dose distribution image as a simulation result is displayed (notified) from the output section 35. Step S5 corresponds to a simulation process.

The operator confirms the dose distribution image displayed on the output section 35. For example, the operator determines whether or not the Bragg peak of the proton beam B accurately reaches a target region (cancer lesion) and whether or not the Bragg peak of the proton beam B does not reach outside the target region (the determination of the simulation result). Here, if it is determined that the Bragg peak of the proton beam B does not accurately reach the cancer lesion, the operator returns the process to Step S4. The operator repeatedly carries out the determination of the irradiation parameters (Step S4) and the dose distribution simulation (S5) until it is determined that the Bragg peak of the proton beam B accurately reaches the cancer lesion. When it is determined that the Bragg peak of the proton beam B accurately reaches the cancer lesion, the operator manipulates the irradiation device 5 to actually irradiate a proton beam (Step S7). Step S7 corresponds to the proton beam irradiation method (charged particle beam irradiation method) which irradiates the proton beam B.

Next, the dose distribution simulation which is performed in the simulation device 3 will be described. The dose distribution simulation is a method which supposes when the proton beam B is irradiated onto the irradiation target X, hypothesizes the proton beam B as a virtual shape having pencil beam-shaped (conical) spread, and simulates the dose distribution of the proton beam B in the irradiation target X by using a dose distribution kernel which derives the spread of the proton beam B in the irradiation target X, and is performed by the DMS-PBA method advanced from the PBA method.

When receiving simulation data, the simulation device 3 performs processing relating to the dose distribution simulation. The input section 31 of the simulation device 3 receives an input of simulation data including CT image data for therapy, irradiation region data, and irradiation parameter data (Step S11).

If simulation data is received by the input section 31, the arithmetic section 33 supposes when the proton beam 13 is irradiated onto the irradiation target X, hypothesizes the proton beam B as a beam (virtual shape) having pencil beam-shaped (conical) spread on the basis of irradiation region data and irradiation parameter data (material information), and the dose distribution kernel, and hypothesizes that the beam is emitted (Step S12).

Next, the arithmetic section 33 computes lateral emittance of the beam to the body surface Xa by using the dose distribution kernel which derives the spread of a beam in the irradiation target X. The arithmetic section 33 also hypothesizes that the beam spread to a predetermined range at an intermediate portion (body surface) in the traveling direction of the beam has reached the body surface Xa, and creates the surface map to the body surface Xa (Step S13).

Next, the arithmetic section 33 segments the surface map in the body surface Xa to hypothesize a plurality of voxels so as to segment the beam in the body surface Xa (Step S14). The arithmetic section 33 also hypothesizes a plurality of beamlets (virtual shape) having pencil beam-shaped (conical) spread with a plurality of voxels as a start point, and hypothesizes that the segmented beamlets have been emitted (Step S15). The arithmetic section 33 also calculates the dose distribution of the proton beam B in the irradiation target X on the basis of CT image data for therapy and a plurality of beamlets (Step S16). With the above, the dose distribution simulation ends.

Next, the effects of the simulation device 3 and the dose distribution simulation method of this embodiment will be described.

For example, when the irradiation target X is made of only a predetermined material, even in the PBA method of the related art, comparatively high precision can be expected. However, since an actual irradiation target X, such as a patient, is made by complicatedly combining various materials, in the PBA method of the related art, it is difficult to calculate the dose distribution of the proton beam (charged particle beam) with good precision. Meanwhile, according to the simulation device 3 and the dose distribution simulation method of this embodiment, the pencil beam (conical) virtual shape hypothesized as the proton beam B is appropriately segmented and hypothesized as a plurality of beamlets (virtual shape). For this reason, it becomes possible to calculate the dose distribution of the proton beam B while coping with the configuration in which the segmented beamlets are complicatedly combined. Therefore, it is effective for improving the precision of the dose distribution.

In the simulation device 3 and the dose distribution simulation method of this embodiment, after the proton beam (charged particle beam) B is hypothesized as the pencil beam (conical) virtual shape, the dose distribution of the proton beam B is obtained. Therefore, it is possible to reduce a burden of arithmetic processing compared to the Monte Carlo simulation in which the dose distribution is derived through statistical arithmetic processing. As a result, it becomes possible to reduce a burden of arithmetic processing while suppressing degradation in precision to quickly calculate the dose distribution.

In this embodiment, the position where the proton beam B is segmented is the position immediately before the proton beam B enters the irradiation target X (body surface Xa). Therefore, it is possible to segment the proton beam B into a plurality of beamlets (virtual shape) to correspond to the internal structure immediately before entering the irradiation target X, making it possible to expect high precision in calculating the dose distribution of the proton beam B.

In this embodiment, the output section 35 is provided to provide notification of the dose distribution calculated by the arithmetic section 33, such that text information, image information, sound information, or the like which can be viewed or heard by the operator can be notified from the output section 35. Therefore, it is possible for the operator to easily recognize the dose distribution of the proton beam B as the simulation result.

The output section 35 outputs the image of the dose distribution in the form of an isodose line or isodose surface to provide notification to the operator, such that it is possible for the operator to easily recognize the magnitude of the dose.

Figure 12:
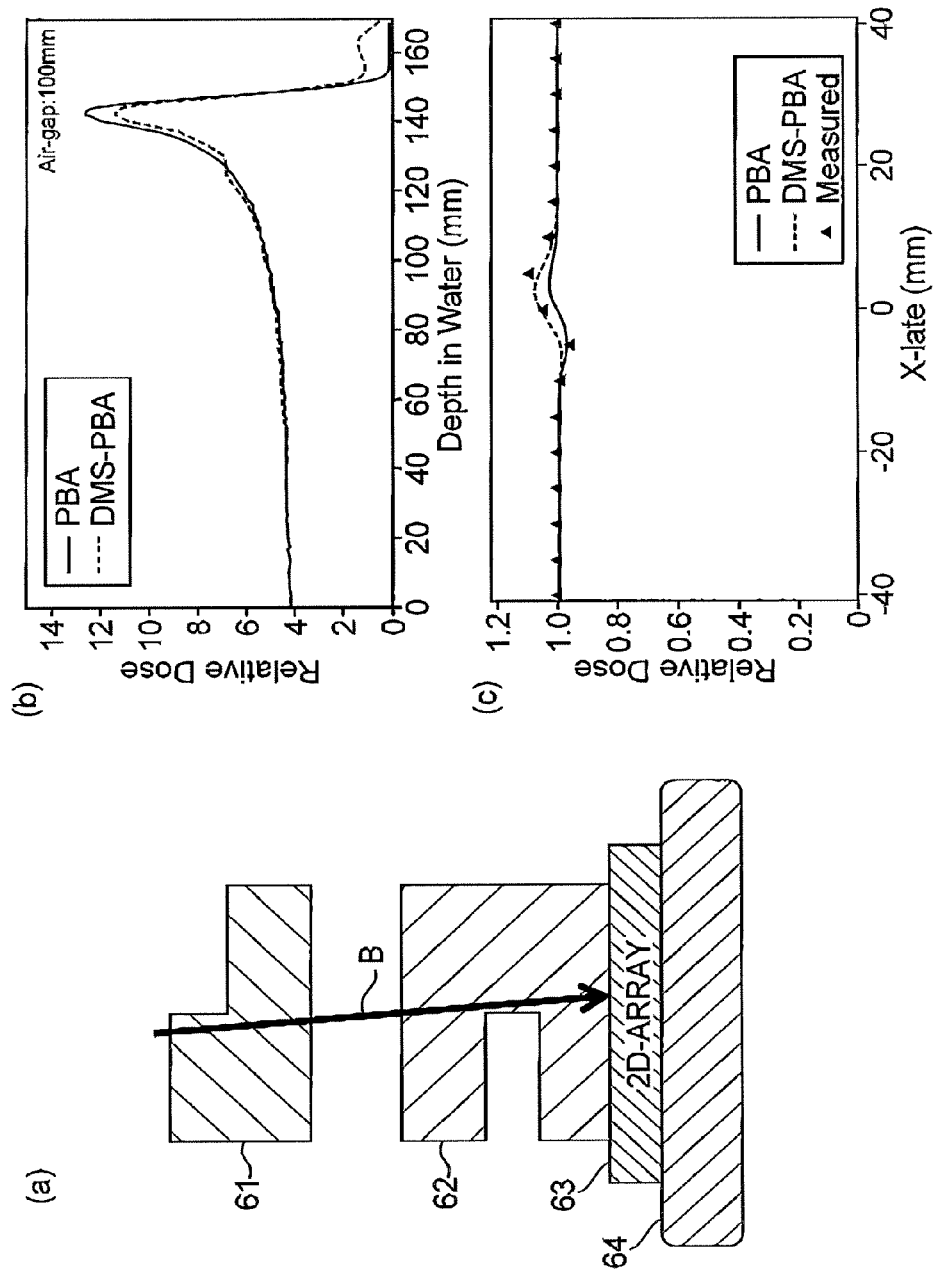
FIGS. 12A to 12C are graphs showing a simulation result of Example 1.
Figure 13:
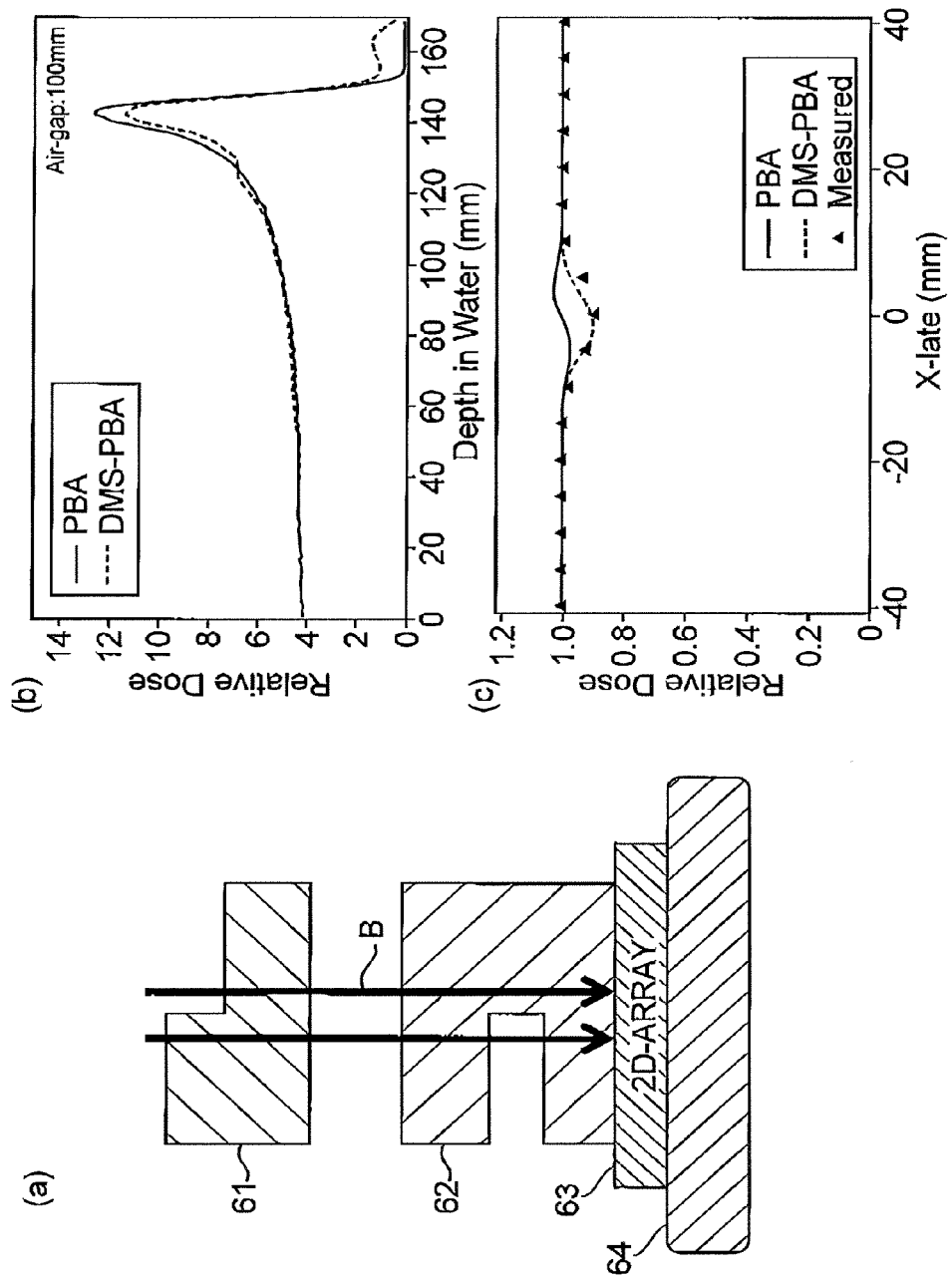
FIGS. 13A to 13C are graphs showing a simulation result of Example 2.
Figure 14:
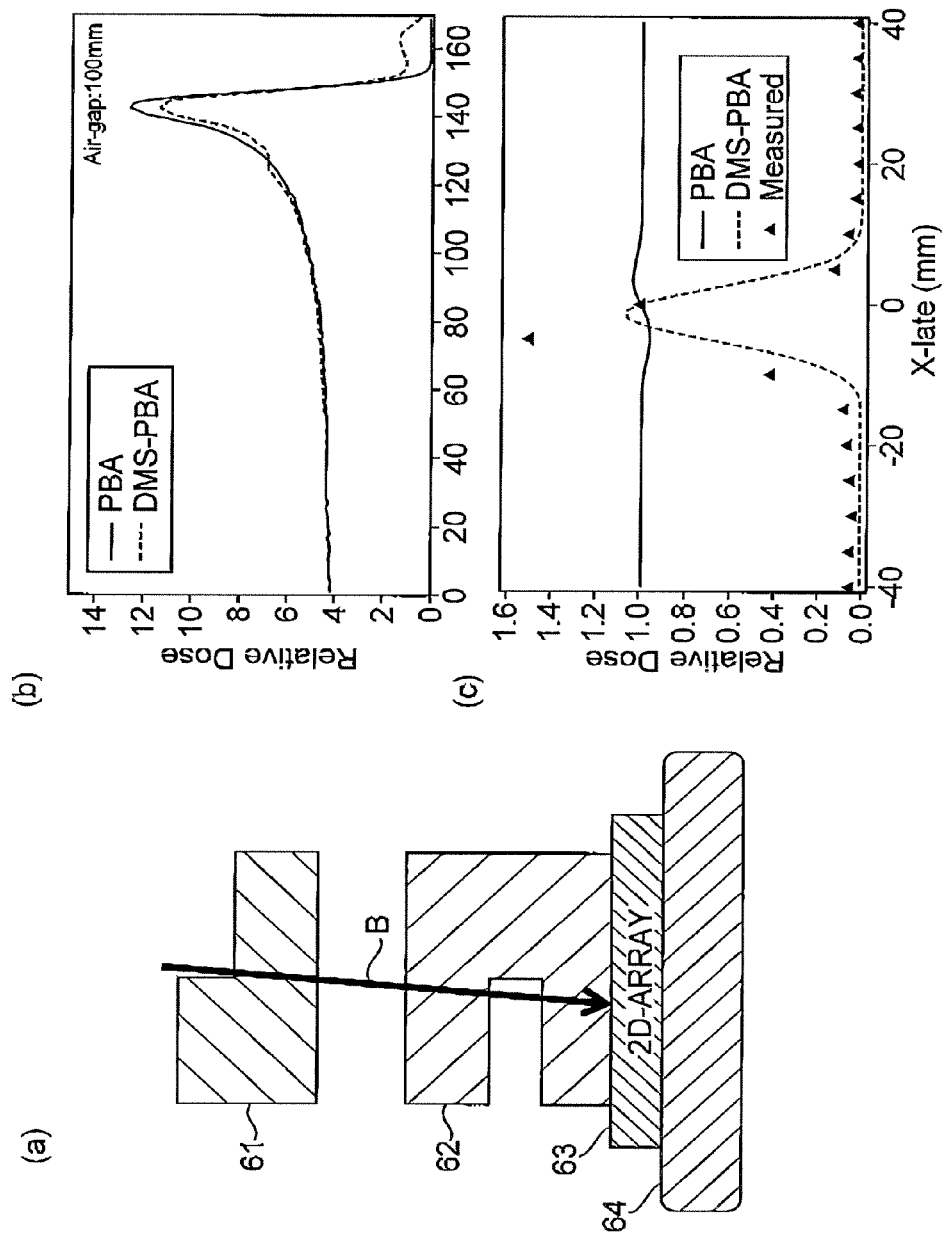
FIGS. 14A to 14C are graphs showing a simulation result of Example 3.

Next, an experiment result for verifying the superiority of this embodiment will be described with reference to FIGS. 12A to 12C, 13A to 13C, and 14A to 14C. FIGS. 12A to 12C, 13A to 13C, and 14A to 14C show a verification result using experimental geometry. FIGS. 12A, 13A, and 14A are diagrams schematically showing the traveling direction of the proton beam B with respect to a phantom which is an irradiation target model. FIGS. 12B, 13B, and 14B are graphs showing a dose distribution profile in the deep portion direction of the irradiation target X. FIGS. 12C, 13C, and 14C are graphs showing a lateral dose distribution profile at a predetermined depth.

In Example 1, Example 2, and Example 3, a verification experiment is carried out by using an experimental apparatus (see FIGS. 12A, 13A, and 14A) which includes a bolus 61 having an L-shaped section, a polystyrene phantom 62 reproducing the boundary between air in a paranasal sinus and a soft tissue, a two-dimensional dosemeter (2D-ARRAY) 63 arranged below the phantom 62, and a patient bed 64 for proton therapy supporting the phantom 62 and the 2D-ARRAY. In Examples 1, 2, and 3, the dose distribution profile is derived by the PBA method and the DMS-PBA method supposing that the beam B has passed through the phantom 62.

As shown in FIGS. 12B, 13B, and 14B, in the simulation results (the dose distribution profile in the deep portion direction) of Example 1, Example 2, and Example 3, with regard to the dose at the Bragg peak, the dose derived by the DMS-PBA method is smaller than the dose derived by the PBA method. FIG. 12C shows a lateral dose distribution profile at the Bragg peak depth (the depth d is 123 mm) in Example 1. A hot spot is observed in the value (Measured) actually measured by the 2D-ARRAY 63 of the above-described experimental apparatus. FIG. 13C shows a lateral dose distribution profile at the Bragg peak depth (the depth d is 142 mm) in Example 2. A cold spot is observed in the actually measured value (Measured). FIG. 14C shows a lateral dose distribution profile at the Bragg peak depth (the depth d is 162 mm) in Example 3. A hot spot is observed in the actually measured value (Measured). A hot spot refers to a spot with a high dose, and a cold spot refers to a spot with a low dose.

Next, the contents which are inferred from the verification results of Example 1, Example 2, and Example 3 will be described.

(1) In Examples 1, 2, and 3, it can be considered that a hot spot or a cold spot at the Bragg peak depth appears due to the influence of the bypass effect of the proton.

(2) In the PBA method, degradation in precision of about maximum 12% was observed at a hot spot or a cold spot of each Bragg peak. It is considered that this situation occurs because the spread pencil beam shape takes into consideration only lateral spread along the center axis.

(3) In the DMS-PBA method, the influence of a heterogeneous material in the body can be taken into consideration through the segmentation of the beam B in the body surface. As a result, it was confirmed that the lateral dose distribution profile is consistent with precision of 3% taking into consideration geometric misalignment of the phantom 62 by about several mm.

The following verification results can be obtained from the results shown in Table 1.

TABLE 1

| Irradiation | PBA | | DMS-PBA | | DMS-PBA/PBA | |
|---|---|---|---|---|---|---|
| Field | Volume | Time | Volume | Time | Volume | Time |
| IF: 30 × 30 | 36.5 | 1.96 | 47 | 2.68 | 1.28 | 1.37 |
| IF: 50 × 50 | 10.1 | 5.26 | 100 | 5.51 | 0.992 | 1.05 |
| IF: 100 × 100 | 40.5 | 20.7 | 318 | 17.4 | 0.785 | 0.838 |

IF: Irradiation Field (mm$^2$)
Volume: total volume (Litter) computed by beam
Time: time (sec) necessary for computation (1) As the irradiation field increases, in both the PBA method and the DMS-PBA method, the computation time (the time for arithmetic processing) is extended.

(2) In the PBA method and the DMS-PBA method, as the ratio of the total volume computed by the beam decreases, the ratio to the computation time also decreases.

(3) When the irradiation field is 100×100 mm$^2$, the computation time in the DMS-PBA method was reduced compared to the computation time in the PBA method.

From the above verification results, it has been confirmed that, compared to the PBA method which is currently mounted in clinical practice, in the DMS-PBA method, the precision of the dose distribution computation result (simulation result) is superior in the heterogeneous region of the phantom 62 for the same computation time.

It has also been confirmed that, though initial verification using a phantom, the DMS-PBA method may be useful in clinical practice.

Although the invention has been described in connection with the simulation device and the dose distribution simulation method of the embodiment, the invention is not limited to the above-described embodiment. For example, a form which is notified from the output section 35 is not limited to predetermined image data, and sound data or the like may be used. The simulation device may not be provided in the proton therapy apparatus and may be provided separately from the proton therapy apparatus.

It should be understood that the invention is not limited to the above-described embodiment, but may be modified into various forms on the basis of the spirit of the invention. Additionally, the modifications are included in the scope of the invention.

What is claimed is:

1. A simulation device which supposes when a plurality of charged particle beams are irradiated onto an irradiation target, hypothesizes the plurality of charged particle beams as a virtual shape having conical spread, and simulates the dose distribution of the plurality of charged particle beams in the irradiation target using a dose distribution kernel which derives the spread of the plurality of charged particle beams in the irradiation target, the simulation device comprising:
    an input unit which receives an input of simulation data including material information of the irradiation target and irradiation information of the plurality of charged particle beams; and
    an arithmetic unit which calculates the dose distribution of the plurality of charged particle beams in the irradiation target on the basis of simulation data received by the input unit and the dose distribution kernel,
    wherein the arithmetic unit segments a plurality of charged particle beams spread to a predetermined range at an intermediate portion in the traveling direction of the plurality of charged particle beams, hypothesizes a plurality of virtual shapes having conical spread with a segmented position as a start point, and calculates the dose distribution of the plurality of charged particle beams in the irradiation target on the basis of simulation data received by the input unit and a plurality of virtual shapes of the plurality of charged particle beams.

2. The simulation device according to claim 1, wherein a position where the plurality of charged particle beams are segmented is a position immediately before the plurality of charged particle beams enter the irradiation target.

3. The simulation device according to claim 1, further comprising:
    an output unit which provides notification of the dose distribution calculated by the arithmetic unit.

4. The simulation device according to claim 3, wherein the output unit provides notification of the dose distribution in the form of an isodose line or isodose surface.

5. A charged particle beam irradiation device comprising: the simulation device according to claim 1.

6. A simulation method which supposes when a plurality of charged particle beams are irradiated onto an irradiation target, hypothesizes the plurality of charged particle beams as a virtual shape having conical spread, and simulates the dose distribution of the plurality of charged particle beams in the irradiation target using a dose distribution kernel which derives the spread of the plurality of charged particle beams in the irradiation target, the simulation method comprising:
    an irradiation target information acquisition step of acquiring material information of the irradiation target;
    an irradiation information setting step of calculating irradiation information of the plurality of charged particle beams; and
    a simulation step of segmenting the plurality of charged particle beams spread to a predetermined range at an intermediate portion in the traveling direction of the plurality of charged particle beams on the basis of the irradiation information calculated in the irradiation information setting step and the dose distribution kernel, hypothesizing a plurality of virtual shapes having conical spread with a segmented position as a start point, and calculating the dose distribution of the plurality of charged particle beams in the irradiation target on the basis of the material information acquired in the irradiation target information acquisition step and a plurality of virtual shapes of the plurality of charged particle beams.

7. A charged particle beam irradiation method comprising irradiating a plurality of charged particle beams on a basis of the dose distribution of the plurality of charged particle beams calculated by the simulation method according to claim 6.

* * * * *